US008415113B1

(12) United States Patent
Heinrich et al.

(10) Patent No.: US 8,415,113 B1
(45) Date of Patent: Apr. 9, 2013

(54) DIAGNOSTIC METHOD FOR DETECTING DISTURBANCES OF THE PANCREAS

(75) Inventors: Hans-Werner Heinrich, Riemserort (DE); Rainer Kleinert, Greifswald (DE); Udo Meyer, Hastorf (DE); Heinz-Jürgen Wagner, Berlin (DE)

(73) Assignee: R-Biopharm AG, Darmstadt (DE)

( * ) Notice: Subject to any disclaimer, the term of this patent is extended or adjusted under 35 U.S.C. 154(b) by 0 days.

(21) Appl. No.: 09/786,725

(22) PCT Filed: Sep. 3, 1999

(86) PCT No.: PCT/DE99/02816
§ 371 (c)(1),
(2), (4) Date: Apr. 23, 2001

(87) PCT Pub. No.: WO00/14542
PCT Pub. Date: Mar. 16, 2000

(30) Foreign Application Priority Data

Sep. 8, 1998 (DE) .................................. 198 40 900
May 25, 1999 (DE) .................................. 199 23 892

(51) Int. Cl.
*C07K 16/40* (2006.01)
*C12P 21/08* (2006.01)
*A61K 38/08* (2006.01)
*A61K 38/10* (2006.01)
*G01N 33/531* (2006.01)
*G01N 33/543* (2006.01)
*G01N 33/573* (2006.01)
*G01N 33/577* (2006.01)
*G01N 33/545* (2006.01)

(52) U.S. Cl. .......... 435/7.4; 435/7.1; 435/7.2; 435/7.94; 435/23; 435/70.21; 435/452; 435/338; 435/975; 436/518; 436/531; 436/547; 436/548; 436/164; 436/811; 514/14; 514/15; 530/327; 530/388.26; 530/389.3; 530/389.7; 530/391.1

(58) Field of Classification Search .................... 435/7.1, 435/7.2, 7.4, 7.94, 70.21, 452, 338, 975; 436/518, 531, 547, 548, 164, 811; 530/388.26, 530/389.3, 389.7, 391.1, 327; 514/14, 15
See application file for complete search history.

(56) References Cited

U.S. PATENT DOCUMENTS 5,622,837 A  4/1997  Scheefers et al. ............. 435/338

FOREIGN PATENT DOCUMENTS

EP  0547059  7/1991

OTHER PUBLICATIONS

Sziegoleit et al., 1989. ELISA for human pancreatic elastase 1. Clin. Biochem. 22: 79-83.*

Geokas et al., 1977. Pancreatic elastase in human serum. J. Biological Chemistry 252: 61-67.*
Tani et al., 1988. Identification of a novel class of elastase isozyme, human pancreatic elastase III, by cDNA and genomic gene cloning. J. Biological Chemistry 263: 1231-1239.*
Schneider et al., 2005. Monoclonal versus polyclonal ELISA for assessment of fecal elastase concentration: pitfalls of a new assay. Clin. Chem. 51: 1052-1054.*
Stein, et al., 1996. Immunoreactive elastase I: clinical evaluation of a new noninvasive test of pancreatic function. Clinical Chemistry 42: 222-226.*
Harlow et al., 1988. Antibodies. A Laboratory Manual, Cold Spring Harbor Laboratory, Cold Spring Harbor. pp. 72-77.*
Weiss et al., 2006. Assessment of isoform specificity of a polyclonal elastase ELISA. Pancreas 33(4): 507.*
Weiss et al., 2006. Assessment of isoform specificity of a polyclonal elastase ELISA. J. Ped. Gastroenterol. Nut. 43: E32, Abstract #58.*
Weiss et al., 2006. Assessment of isoform specificity for a polyclonal elastase ELISA. Pancreatology 6: 343, Abstract P3.*
Detection of Pancreativ Elastase 3A and 3B by a polyclonal Elastase ELISA F U Weiss, M Ruthenburger, J. Gebel, E Hammer, U Volker, M M Lerch M2182 DDW May 19-24, 2007, Washington Convention Center.
Pancreatology 2006; 6:323-405 Published online: Jun. 6, 2006 DOI: 10.1159/000093601 38th European Pancreatic Club (EPC) Meeting.
Journal of Pediatric Gastroenterology and Nutrition 43: E14-E76 Oct. 2006 Lippioncott Williams & Wilkins, Philadelphia North American Society for Pediatric Gastroenterology, Hepatology, and Nutrition Annual Meeting Oct. 19-22, 2006 Orlando, Florida.
Abstracts: Abstracts of Papers Submitted to the 37th Annual Meeting of the American Pancreatic Association and 13th Meeting of the International Association of Pancreatology Nov. 1-4, 2006 Chicago, Illinois.
Weiss et al. Pancreas vol. 33, No. 4, Nov. 2006, p. 507.
Specificity of the Polyclonal Antibody Test System for Human Elastase in Stool C M Qualia 1, JF Villalona1, C Ren2, T M Rossi1, Published in: Journal of Pediatric Gastroenterology and Nutrition, vol. 45:E26 #66, No. 4 Oct. 2007, Abstract only.
Evolutionary silencing of the human elastase I gene (ELA1) Scott D. ARose and Raymond J. MacDonald 1997 Oxford University Press, Human Molecular Genetics, 1997, vol. 6, No. 6 p. 897-903.
Weiss et al., Assessment of Isoform specificity for a polyclonal Elastase ELISA, J. Ped. Gastroenterol. Nut. 43: E32 #58, 2006. Abstract only.
List of Abstracts; Synopsis of publications concerning the Pancreatic Elastase Test according to U.S. Appl. No. 09/786,725 (Applicant: Bioserv), Bioserv Diagnostics.

(Continued)

*Primary Examiner* — Gail R Gabel
*Assistant Examiner* — James L Grun
(74) *Attorney, Agent, or Firm* — Norris McLaughlin & Marcus, P.A.

(57) ABSTRACT

A procedure for the identification of a functional disorder of the pancreas by the use of parts of all iso-enzymes of the pancreas elastase and of synthetic amino-acid sequences as antigens for obtaining specific antibodies, as well as their use in immuno-chemical test procedures.

15 Claims, No Drawings

OTHER PUBLICATIONS

Erickson et al., Clinica Chimica Acta 397 (2008) 87-91 Evaluation of a fecal pancreatic elastase-1 enzyme-linked immunosorbent assay: Assessment versus an established assay and implication in classifying pancreatic function.

Garcia-Bueno et al., Quantification of fecal Elastase-1 using either polyclonal or monoclonal antibodies, 2002. Gastroenterol. 122:A510, Abstract.

Clin. Lab. 2003;49:209-215; Original Article Clinical Value of a New Fecal Elastase Test for Detection of Chronic Pancreatitis Volker Keim, Niels Teich, and Joachim Moessner.

Lankisch et al., www.bioserv-diagnostics.com Overview publications Sep. 15, 2004 (3 pages).

* cited by examiner

DIAGNOSTIC METHOD FOR DETECTING DISTURBANCES OF THE PANCREAS

This application is a Sec. 371 application of PCT/DE99/02816, filed Sep. 3, 1999, claiming the priority of German national applications DE 19840900.1, filed Sep. 8, 1998, and DE 19923892.8, filed May 25, 1999.

BACKGROUND OF THE INVENTION

The invention relates to a diagnostic procedure for the recognition of a functional disorder of the pancreas. The areas of application are medicine and the pharmaceutical industry.

Functional disorders of the pancreas may be the result of various illnesses whose diagnosis should be underpinned by the definition of functional criteria. The most frequent diseases of the pancreas are chronically recurrent and acute pancreatitis.

Chronic pancreatitis is an insidious progressive disease in which functioning pancrease tissue gradually degenerates in a scleroticising process. It is characterised by its clinical symptoms (abdominal complaints, steatorrhoea, weight loss), typical morphological changes of the gland (calcification, dilated and irregularly demarcated Ductus pancreaticus) and by a progressive exocrine and endocrine loss of function (indigestion, diabetes mellitus). The incidence of chronic pancreatitis is 6 or 8 new cases per 100 000 persons per annum in West Europe. The diagnosis of chronic pancreatitis is becoming increasingly frequent as a result of increasing alcohol consumption.

A number of functional criteria can be identified for the underpinning of clinical and morphological diagnoses. The most sensitive method of analysis is the Secretin-Caerulin or Secretin-Cholecystocinin test, which is, however, unpleasant for the patient and very time-consuming. Indirect test methods that are used include the Lundh-, NBT-PABA- and Pancreoauryl-tests. The identification of trypsin in serum or of chymotrypsin in stool is also of a certain practical significance. The disadvantage that is common to all these indirect test methods is their lack of specificity.

Of all the indirect function tests, the identification of Elastase 1 is the test with the highest sensitivity and specificity (Löser, C., Therapie & Erfolg 1997; 1:411-413). It has become established in daily practice as the standard test for exocrine pancreas function diagnostics. The basis for this test consists of polyclonal antibodies against Elastase 1 (Elastase 1-RIA, Abbott) or mono- and/or polyclonal anti-Elastase-1 antibodies, which are obtained by immunisation with an antigen containing the amino-acid sequence Thr-Met-Val-Ala-Gly-Gly Asp-Ile-Arg (SEQ ID NO: 1) or immunologically effective partial peptides of this. (EP 0 547 059 B1).

Pancreas-Elastase is a proteolytic digestion enzyme. Compared with the common parameters of pancreas diagnostics (e.g. chymotrypsin activity in stool), quantitative Elastase identification has crucial advantages. The enzyme is formed exclusively in the pancreas and displays extraordinary stability during the passage through the intestines, i.e. the concentration of Elastase reflects the secretion performance of the pancreas.

Despite its superiority to other exocrine parameters, the traditional Elastase 1-ELISA methods fail in too many cases to identify pancreas elastase, even though it is present in substantial concentrations.

SUMMARY OF THE INVENTION

The object of the invention is therefore to develop a more sensitive procedure for the recognition of a functional disorder of the pancreas on the basis of the identification of pancreatic elastase.

By means of the systematic examination of stool samples which did not react to elastase 1 using the traditional ELISA method, it was possible after electrophoretic separation to produce samples containing elastase. Further characterisation showed that these proteins were various iso-enzymes, which are obviously not identified by the antibodies in commercial tests. This enzyme is clearly subject to marked genetic polymorphism, which is also reflected in the specialist literature in the description of pancreas elastase 1, 2 and 3. Our own tests showed that at least two iso-enzymes can appear simultaneously. It was also possible to show that these elastases in their concentration dependence to pancreas damage reacted in exactly the same way as elastase 1.

In contrast to the familiar solutions, which are restricted to the specific identification of pancreas elastase 1, it was surprisingly discovered that by the identification of all the pancreas elastase iso-forms, of which pancreas elastases 1, 2 and 3 are currently known, the diagnostic relevance with regard to pancreatic function could be significantly improved. The invention therefore relates to a procedure for producing anti-elastase antibodies in the usual way. However, this procedure is characterised by the fact that the specific antigens used either singly or in combination represent all known elastase iso-enzymes or partial elements of such enzymes or cross-reacting synthetic sequences.

Partial elements are ideally obtained by means of peptide synthesis, with the amino-acid sequence being derived beforehand from the overall sequence by using structural analysis methods or alternatively being identified according to protein sequencing. Although the peptides alone can trigger antibody induction, it proved appropriate in terms of the invention to link these peptides to common carrier substances such as haemocyanine. It is possible with the peptides in the invention to produce monoclonal and polyclonal antibodies.

For the production of the polyclonal anti-peptide antibodies in the invention, animals such as rabbits, guinea pigs, goats, chickens or fish are immunized with the peptides in the familiar way. For the production of monoclonal antibodies, the peptides are used in the familiar way for the induction of specific B-cells, which after fusion with myeloma cells produce hybridoma cells, which then according to familiar cloning procedures are cultivated in cell lines which secrete specific monoclonal antibodies. The mono- or polyclonal antibodies in the invention react only with the used specific epitopes or with well-known elastase iso-enzymes.

It was shown that antibodies against the peptides A-V-K-E-G-P-E-Q-V-I-P-I-N (SEQ ID NO: 2), Y-T-N-G-P-L-P-D-K-L-Q-Q-A-R (SEQ ID NO: 3), R-S-G-C-N-G-D-S-G-G-P-L-N (SEQ ID NO: 4), G-P-L-N-C-P-T-E-D-G-G-W-Q (SEQ ID NO: 5), G-T-E-A-G-R-N-S-W-P-S-Q-I (SEQ ID NO: 6), H-N-L-S-Q-N-D-G-T-E-Q-Y-V (SEQ ID NO: 7), W-G-K-T-K-T-N-G-Q-L-A (SEQ ID NO: 8), V-S-S-R-G-C-N-V-S-R-K-P-T (SEQ ID NO: 9), G-G-E-E-A-R-P-N-S-W-P-W-Q (SEQ ID NO: 10), S-S-S-R-T-Y-R-V-G-L-G-R-H-N (SEQ ID NO: 11), K-D-W-N-S-N-Q-I-S-K-G-N-D (SEQ ID NO: 12), G-P-L-N-C-Q-A-S-D-G-R-W (SEQ ID NO: 13), G-A-L-P-D-D-L-K-Q-G-R-L (SEQ ID NO: 14), S-L-Q-Y-E-K-S-G-S-F-Y (SEQ ID NO 15), F-G-C-N-T-R-R-K-P-T-V-F-T (SEQ ID NO: 16) react highly specifically with the iso-forms of the pancreas elastase and do not react unspecifically with other stool components.

Another subject of the invention is the use of the elastase antibodies in the invention for the identification and quantification of all known elastase iso-enzymes in body fluids and in stool. The invention is therefore also relevant in terms of identification systems, particularly an immunochemical identification system to establish the functionality of the pancreas as an aid to the recognition of functional disorders of this organ. For this purpose the specific antibodies can be connected to a suitable carrier adsorptively or chemically using familiar coupling procedures. Membranes or particles are suitable carriers. The Sandwich-ELISA of the invention can be used with cross-reactive epitope antibodies or a combination of various epitope antibodies to identify and to quantify pancreas elastase in stool and in serum or plasma quickly and specifically.

It can also be used for the diagnosis or to establish the absence of pancreas involvement in abdominal complaints and exocrine pancreas insufficiency.

There are also cases in which the detection of elastase 1 is in itself sufficient to permit a certain diagnosis of pancreas disorders. In such instances, the procedure in the invention is carried out as follows:

The DNA-sequence for human elastase 1 (JP 1987000276-A/6) was transferred to the amino-acid sequences. With the aid of common protein structure programmes, it was possible to identify several amino-acid sequences that displayed a potential epitope structure. It was shown that antibodies against the peptides A-V-K-E-G-P-E-Q-V-I-P-I-N (SEQ ID NO: 2), Y-T-N-G-P-L-P-D-K-L-Q-Q-A-R (SEQ ID NO: 3), R-S-G-C-N-G-D-S-G-G-P-L-N (SEQ ID NO: 4) and G-P-L-N-C-P-T-E-D-G-G-W-Q (SEQ ID NO: 5) bind elastase 1 highly specifically and do not react unspecifically with other stool components.

The invention relates to a procedure for the production of anti-elastase antibodies in the usual way. The distinguishing characteristic is that the specific antigens used have previously been derived from the amino-acid sequence and chemically synthesised by methods of structural analysis. The invention also makes it possible to use parts of these synthetic peptides for the production of antibodies. Although the peptides alone trigger antibody induction, it has proven to be appropriate to connect these peptides to common carrier substances such as haemocyanine. It is possible to produce both monoclonal and polyclonal antibodies from the peptides used in the invention.

Animals such as rabbits, guinea pigs, goats, chickens and fish were immunised with peptides in the usual way in order to produce the polyclonal antipeptide antibodies in the invention. For the production of monoclonal antibodies, the peptides are used in the familiar way for the induction of specific B-cells, which after fusion with myeloma cells generate hybridoma cells, which according to familiar cloning procedures are cultivated in cell lines which secrete specific monoclonal antibodies. The mono- and polyclonal antibodies in the invention react only with the specific epitope used or with mature elastase 1.

The invention includes, without limitation, the following items 1-18:

1. Diagnostic procedure for identification of a disorder of the pancreas by determining the overall content of all known pancreatic elastases (iso-enzymes) in the serum, secretions or excretions of a patient.
2. Procedure according to item 1, characterised by the fact that identification is by means of immuno-chemical systems using monclonal or polyclonal antibodies that can singly and specifically or cross-reactively recognise all elastase iso-enzymes with the amino-acid sequence Thr-Met-Val-Ala-Gly-Gly-Asp-Ile-Arg (SEQ ID NO:1).
3. Procedure according to item 2, characterised by the fact that the antibodies used are obtained by means of antigenes consisting of the complete elastases 1, 2 and 3 or of their sub-units. The amino-acid sequence Thr-Met-Val-Ala-Gly-Gly-Asp-Ile-Arg (SEQ ID NO:1) is not used as an elastase fragment or as an immunologically effective partial sequence thereof
4. Procedure according to item 3, characterised by the fact that the following synthetic peptides are primarily used as antigenes which after the immunisation of animals induce antibodies which cross-reactively recognise several elastases but do not concern the amino-acid sequence Thr-Met-Val-Ala-Gly-Gly-Asp-Ile-Arg (SEQ ID NO:1):
NH2-A-V-K-E-G-P-E-Q-V-I-P-I-N-COOH (SEQ ID NO:2)
NH2-Y-T-N-G-P-L-P-D-K-L-Q-Q-A-R-COOH (SEQ ID NO:3)
NH2-R-S-G-C-N-G-D-S-G-G-P-L-N-COOH (SEQ ID NO:5)
NH2-G-P-L-N-C-P-T-E-D-G-G-W-Q-COOH (SEQ ID NO:4)
NH2-G-T-E-A-G-R-N-S-W-P-S-Q-I-COOH (SEQ ID NO:6)
NH2-H-N-L-S-Q-N-D-G-T-E-Q-Y-V-COOH (SEQ ID NO:7)
NH2-W-G-K-T-K-T-N-G-Q-L-A-COOH (SEQ ID NO:8)
NH2-V-S-S-R-G-C-N-V-S-R-K-P-T-COOH (SEQ ID NO:9)
NH2-G-G-E-E-A-R-P-N-S-W-P-W-Q-COOH (SEQ ID NO:10)
NH2-S-S-S-R-T-Y-R-V-G-L-G-R-H-N-COOH (SEQ ID NO:11)
NH2-K-D-W-N-S-N-Q-I-S-K-G-N-D-COOH (SEQ ID NO:12)
NH2-G-P-L-N-C-Q-A-S-D-G-R-W-COOH (SEQ ID NO:13)
NH2-G-A-L-P-D-D-L-K-Q-G-R-L-COOH (SEQ ID NO:14)
NH2-S-L-Q-Y-E-K-S-G-S-F-Y-COOH (SEQ ID NO:15)
NH2-F-G-C-N-T-R-R-K-P-T-V-F-T-COOH (SEQ ID NO:16)
5. Procedure according to items 1-5, characterised by the fact that antibodies are used singly or in a combination in an immuno-chemical identification system.
6. Immunological test kits for the diagnosis and progress check of diseases of the pancreas using stool or body fluids containing one or more of the antibodies used in items 2-5.
7. Procedure for obtaining monoclonal and/or polyclonal antibodies that react specifically with human elastase 1 in stool or body fluids and are induced by the usual immunisation procedures, characterised by the fact that the peptides A-V-K-E-G-P-E-Q-V-I-P-I-N (SEQ ID NO:2), Y-T-N-G-P-L-P-D-K-L-Q-Q-A-R (SEQ ID NO:3), R-S-G-C-N-G-D-S-G-G-P-L-N (SEQ ID NO:5) and G-P-L-N-C-P-T-E-D-G-G-W-Q (SEQ ID NO:4) or immunogenic partial peptides thereof are used as antigenes for the immunisation of vertebrates, especially of small mammals and birds.
8. Procedure according to item 7, characterised by the fact that before immunisation the free peptides are coupled with suitable carrier substances, primarily haemocyanine or albumin.
9. Procedure according to items 7 and 8, characterised by the fact that polyclonal antibodies are produced using chickens as experimental animals.
10. Polyclonal antibodies, insofar as they were produced according to items 7 to 9.
11. Monoclonal antibodies, insofar as they were produced according to items 7 and 8.
12. Peptide A-V-K-E-G-P-E-Q-V-I-P-I-N (SEQ ID NO:2).
13. Peptide Y-T-N-G-P-L-P-D-K-L-Q-Q-A-R (SEQ ID NO:3).

14. Peptide R-S-G-C-N-G-D-S-G-G-P-L-N (SEQ ID NO:5).
15. Peptide G-P-L-N-C-P-T-E-D-G-G-W-Q (SEQ ID NO:4).
16. Purification and detection systems for human elastase 1, characterised by the fact that they contain at least one of the invention antibodies according to items 10 and 11.
17. Immunological test kits for the diagnosis and progress check of diseases of the pancreas and of mucoviscidosis using stool or body fluids.
18. Immunological test kits according to item 17, characterised by the fact that 2 different antibodies are used (Sandwich-ELISA).

A further subject of the invention is the use of the elastase 1-epitope-specific antibodies for the identification and quantification of elastase 1 in body fluids and in stool. The invention is therefore also relevant to an immuno-chemical identification system for establishing the functionality of the pancreas as an aid to the identification of functional disorders of this organ. The specific antibodies can for this purpose be connected adsorptively or chemically to any suitable carrier using familiar coupling methods. Membranes or particles are suitable carriers. With the aid of the Sandwich-ELISA in the invention in conjunction in each case with two different epitope antibodies, it is possible to identify and to quantify elastase 1 in stool and in serum or plasma quickly and specifically.

IMPLEMENTATION EXAMPLE 1

Production of Specific Anti-Peptide Antibodies which are Targeted Against Definite Segments of Mature Human Elastase 1

Using the fixed-phase synthesis according to Merrifield, peptides with the amino-acid sequences $NH_2$-A-V-K-E-G-P-E-Q-V-I-P-I-N-COOH (SEQ ID NO: 2), $NH_2$-Y-T-N-G-P-L-P-D-K-L-Q-Q-A-R-COOH (SEQ ID NO: 3), $NH_2$-R-S-G-C-N-G-D-S-G-G-P-L-N-COOH (SEQ ID NO: 4) and $NH_2$-G-P-L-N-C-P-T-E-D-G-G-W-Q-COOH (SEQ ID NO: 5) were synthesised. By means of familiar procedures, the peptides are coupled with common limpet haemocyanine (KLH)-(1 mg peptide/mg KLH). In each case, 300 µg of this conjugate with the addition of a Freund adjuvant are used for the immunisation of a rabbit or a chicken. After three vaccinations, the animals are bled. After the serum is obtained, the specificity of the anti-serum is tested in an ELISA. For this purpose free peptide is adsorbed on to the surface of the cavities of microtitre plates. After the incubation of the cavities with the antiserums, they are thoroughly washed. Antigen-antibody reactions are detected in the usual way using an anti-rabbit or anti-chicken POD conjugate and TMB as a substrate. Every antiserum reacts only with the homologous peptide.

IMPLEMENTATION EXAMPLE 2

Proof of the Specificity of the Antibodies in the Invention

Elastase 1 specificity can be demonstrated in the Western blot. Here coarsely and highly purified elastase 1 from stool is separated from accompanying impurities by means of polyacrylamide gel electrophoresis according to their relative molecular mass. The protein zones from the gel are transferred to nitro cellulose by means of a "Semi-dry-blotting" apparatus. After saturation of the free binding sites of the membrane with re-suspended dried skimmed milk, the membranes are incubated with the anti-peptide antiserums diluted at a rate of 1:500. After intensive washing of the membranes to remove all unspecifically-bound antibodies, the membranes are incubated with anti-rabbit antibodies marked with phosphatase. The specifically-bound secondary antibodies that remain on the membrane after washing are made visible after the substrate has been added. This shows that only elastase was identified in the sample used.

IMPLEMENTATION EXAMPLE 3

Identification of Elastase 1 in Stool Using the Invention Antibody in an ELISA

The elastase 1 in serum samples or in stool samples is identified in a fixed phase enzyme immuno-assay based on the sandwich technique. A polyclonal antibody that is targeted against epitopes of elastase 1 is dissolved in a carbonate/bicarbonate buffer solution pH 9.6 and placed in the wells of a microtiter plate. After incubation at 4° C. over 12 h, the non-bound antibodies are removed by washing with PBS. The still-free binding sites of the carrier material are blocked by a PBS buffer containing ethanolamine and Tween 20. Blocking occurs over a 90 minute period at room temperature. After washing, the serum or stool samples diluted in PBS are placed in the wells via pipettes. The 60-minute incubation at room temperature is ended by washing. A second elastase 1-specific polyclonal antibody that is conjugated with biotin is added to the elastase that is connected to the first antibody.

After an incubation of 30 minutes and the washing process, the biotin-marked antibody with peroxidase-conjugated streptavidin is identified. The non-connected streptavidin is removed in the final washing phase. TMB is added as a substrate for the peroxidase and after a defined time the colour reaction is stopped by the addition of HCl. The alteration in optical density is measured. The intensity of the colour reaction is proportional to the elastase 1 concentration of the sample.

IMPLEMENTATION EXAMPLE 4

Production of Specific Anti-Peptide Antibodies which are Targeted Against Defined Segments of Iso-Forms of Pancreas Elastase Using fixed-phase synthesis according to Merrifield, the peptides are synthesised with the amino-acid sequences A-V-K-E-G-P-E-Q-V-I-P-I-N (SEQ ID NO: 2), Y-T-N-G-P-L-P-D-K-L-Q-Q-A-R (SEQ ID NO: 3), R-S-G-C-N-G-D-S-G-G-P-L-N (SEQ ID NO: 4), G-P-L-N-C-P-T-E-D-G-G-W-Q (SEQ ID NO: 5), G-T-E-A-G-R-N-S-W-P-S-Q-I (SEQ ID NO: 6), H-N-L-S-Q-N-D-G-T-E-Q-Y-V (SEQ ID NO: 7), W-G-K-T-K-T-N-G-Q-L-A (SEQ ID NO: 8), V-S-S-R-G-C-N-V-S-R-K-P-T (SEQ ID NO: 9), G-G-E-E-A-R-P-N-S-W-P-W-Q (SEQ ID NO: 10), S-S-S-R-T-Y-R-V-G-L-G-R-H-N (SEQ ID NO: 11), K-D-W-N-S-N-Q-I-S-K-G-N-D (SEQ ID NO: 12), G-P-L-N-C-Q-A-S-D-G-R-W (SEQ ID NO: 13), G-A-L-P-D-D-L-K-Q-G-R-L (SEQ ID NO: 14), S-L-Q-Y-E-K-S-G-S-F-Y (SEQ ID NO: 15), F-G-C-N-T-R-R-K-P-T-V-F-T (SEQ ID NO: 16). The peptides are coupled to common limpet haemocyanine (KLH) using the familiar procedure (1 mg peptide/mg KLH). In each case 300 µl of this conjugate with the addition of a Freund adjuvant are used for the immunisation of a rabbit or a chicken. After three vaccinations, the animals are bled. After obtaining the antibodies (purification via a protein A pillar or by fractional precipitation), their specificity is tested in an ELISA. For this purpose free peptide is adsorbed on to the surface of the cavities of microtiter plates. After the incubation of the cavities with the homolo-

IMPLEMENTATION EXAMPLE 5

Proof of the Specificity of the Antibody in the Invention

The specificity of the antibodies for various iso-forms of the pancreas elastase can be demonstrated in the Western blot. For this purpose coarsely and highly purified elastase samples from stool and pancreatic juice are separated from accompanying impurities by means of polyacrylamide gel electrophoresis according to their relative molecular mass. The protein zones from the gel are transferred to nitrocellulose with the aid of a "semi-dry" blotting apparatus. After saturation of the free connecting places of the membrane with re-suspended dry skimmed milk, the membranes are then incubated with the pre-diluted anti-peptide antibodies either alone or in various combinations. After intensive washing of the membranes to remove all unspecifically bound antibodies, the membranes with alkaline phosphatase-marked anti-rabbit antibodies are incubated in a previously established concentration. The specific secondary antibodies remaining on the membrane after washing are made visible after the addition of substrate. It was shown that elastase can be detected in all samples with individual antibodies or antibody mixtures but that not every antibody detects all iso-forms.

IMPLEMENTATION EXAMPLE 6

Identification of the Pancreas Elastase in Stool and Serum Using the Antibodies in the Invention The elastase in serum, plasma or stool is identified using a fixed-phase ELISA based on the sandwich technique. For this purpose individual invention antibodies or a corresponding mixture of several of the invention antibodies are dissolved in a carbonate/bicarbonate buffer solution pH 9.6 and placed in the wells of a microtiter plate. After incubation at 4° C., the non-bound antibodies are removed by washing with PBS. The remaining free connecting places of the carrier substance are blocked by an ethanolamine/Tween 20-PBS buffer. Blocking takes place at room temperature over 90 minutes. After washing, the serum or stool samples diluted in PBS are placed in the wells via pipettes. The 60-minute incubation at room temperature is ended by washing. Individual invention antibodies or a mixture of several invention antibodies conjugated with biotin are used as detection antibodies. After a 30-minute incubation and the washing process, the biotin-marked antibody is identified with peroxidase-conjugated streptavidin. In the final washing step, the non-bound streptavidin is removed. Next the peroxidase concentration is established with TMB as a substrate. After the addition of HCl to end the enzyme reaction, the alteration of the optical density is measured. The intensity of the colour reaction is proportional to the elastase concentration in the sample.

---

SEQUENCE LISTING

```
<160> NUMBER OF SEQ ID NOS: 16

<210> SEQ ID NO 1
<211> LENGTH: 9
<212> TYPE: PRT
<213> ORGANISM: Homo sapiens

<400> SEQUENCE: 1

Thr Met Val Ala Gly Gly Asp Ile Arg
1               5

<210> SEQ ID NO 2
<211> LENGTH: 13
<212> TYPE: PRT
<213> ORGANISM: Homo sapiens

<400> SEQUENCE: 2

Ala Val Lys Glu Gly Pro Glu Gln Val Ile Pro Ile Asn
1               5                   10

<210> SEQ ID NO 3
<211> LENGTH: 14
<212> TYPE: PRT
<213> ORGANISM: Homo sapiens

<400> SEQUENCE: 3

Tyr Thr Asn Gly Pro Leu Pro Asp Lys Leu Gln Gln Ala Arg
1               5                   10

<210> SEQ ID NO 4
<211> LENGTH: 13
<212> TYPE: PRT
<213> ORGANISM: Homo sapiens
```

The text "gous or heterologous antibodies, the cavities are thoroughly cleaned. The antigen-antibody reactions are detected in the usual way using anti-rabbit or anti-chicken POD conjugates. Every antibody reacts only with the homologous peptide." appears at the top of the left column before IMPLEMENTATION EXAMPLE 5.

```
<400> SEQUENCE: 4

Gly Pro Leu Asn Cys Pro Thr Glu Asp Gly Gly Trp Gln
1               5                   10

<210> SEQ ID NO 5
<211> LENGTH: 13
<212> TYPE: PRT
<213> ORGANISM: Homo sapiens

<400> SEQUENCE: 5

Arg Ser Gly Cys Asn Gly Asp Ser Gly Gly Pro Leu Asn
1               5                   10

<210> SEQ ID NO 6
<211> LENGTH: 13
<212> TYPE: PRT
<213> ORGANISM: Homo sapiens

<400> SEQUENCE: 6

Gly Thr Glu Ala Gly Arg Asn Ser Trp Pro Ser Gln Ile
1               5                   10

<210> SEQ ID NO 7
<211> LENGTH: 13
<212> TYPE: PRT
<213> ORGANISM: Homo sapiens

<400> SEQUENCE: 7

His Asn Leu Ser Gln Asn Asp Gly Thr Glu Gln Tyr Val
1               5                   10

<210> SEQ ID NO 8
<211> LENGTH: 11
<212> TYPE: PRT
<213> ORGANISM: Homo sapiens

<400> SEQUENCE: 8

Trp Gly Lys Thr Lys Thr Asn Gly Gln Leu Ala
1               5                   10

<210> SEQ ID NO 9
<211> LENGTH: 13
<212> TYPE: PRT
<213> ORGANISM: Homo sapiens

<400> SEQUENCE: 9

Val Ser Ser Arg Gly Cys Asn Val Ser Arg Lys Pro Thr
1               5                   10

<210> SEQ ID NO 10
<211> LENGTH: 13
<212> TYPE: PRT
<213> ORGANISM: Homo sapiens

<400> SEQUENCE: 10

Gly Gly Glu Glu Ala Arg Pro Asn Ser Trp Pro Trp Gln
1               5                   10

<210> SEQ ID NO 11
<211> LENGTH: 14
<212> TYPE: PRT
<213> ORGANISM: Homo sapiens

<400> SEQUENCE: 11
```

```
Ser Ser Ser Arg Thr Tyr Arg Val Gly Leu Gly Arg His Asn
1               5                   10

<210> SEQ ID NO 12
<211> LENGTH: 13
<212> TYPE: PRT
<213> ORGANISM: Homo sapiens

<400> SEQUENCE: 12

Lys Asp Trp Asn Ser Asn Gln Ile Ser Lys Gly Asn Asp
1               5                   10

<210> SEQ ID NO 13
<211> LENGTH: 12
<212> TYPE: PRT
<213> ORGANISM: Homo sapiens

<400> SEQUENCE: 13

Gly Pro Leu Asn Cys Gln Ala Ser Asp Gly Arg Trp
1               5                   10

<210> SEQ ID NO 14
<211> LENGTH: 12
<212> TYPE: PRT
<213> ORGANISM: Homo sapiens

<400> SEQUENCE: 14

Gly Ala Leu Pro Asp Asp Leu Lys Gln Gly Arg Leu
1               5                   10

<210> SEQ ID NO 15
<211> LENGTH: 11
<212> TYPE: PRT
<213> ORGANISM: Homo sapiens

<400> SEQUENCE: 15

Ser Leu Gln Tyr Glu Lys Ser Gly Ser Phe Tyr
1               5                   10

<210> SEQ ID NO 16
<211> LENGTH: 13
<212> TYPE: PRT
<213> ORGANISM: Homo sapiens

<400> SEQUENCE: 16

Phe Gly Cys Asn Thr Arg Arg Lys Pro Thr Val Phe Thr
1               5                   10
```

The invention claimed is:

1. A diagnostic method for determining pancreatic function in a human patient, the method comprising the steps of:
providing two or more different purified polyclonal antibodies each elicited against an immunogenic composition comprising a conjugate consisting of a non-elastase carrier protein and one or more synthetic peptides selected from the group consisting of
NH2-A-V-K-E-G-P-E-Q-V-I-P-I-N-COOH (SEQ ID NO: 2),
NH2-Y-T-N-G-P-L-P-D-K-L-Q-Q-A-R-COOH (SEQ ID NO: 3),
NH2-G-P-L-N-C-P-T-E-D-G-G-W-Q-COOH SEQ ID NO: 4), and
NH2-R-S-G-C-N-G-D-S-G-G-P-L-N-COOH (SEQ ID NO: 5);
wherein said different antibodies are each specific for human pancreatic elastase 1;
obtaining a sample of a bodily fluid or stool from the patient;
mixing the sample with the two or more different purified antibodies to form specific immune complexes among the antibodies and human pancreatic elastase 1 present in the sample; and
detecting an amount of the immune complexes to determine an amount of human pancreatic elastase 1 in the sample, wherein the amount of human pancreatic elastase 1 in the sample is indicative of pancreatic function in the patient.

2. The diagnostic method of claim 1 wherein the bodily fluid sample is a sample of serum, plasma, or pancreatic juice.

3. The diagnostic method of claim 1 wherein the sample is a stool sample.

4. The diagnostic method of claim 1 wherein two or more different purified polyclonal antibodies specific for human pancreatic elastase 1 are provided and the method is a sandwich enzyme linked immunosorbent assay wherein the sample is brought into contact with a) a solid phase carrier-immobilized at least one of said antibodies, and b) a detectably-labeled at least different one of said antibodies.

5. A diagnostic kit for determining a disorder of pancreatic function or determining mucoviscidosis in a human patient comprising:
two or more different purified polyclonal antibodies each elicited against an immunogenic composition comprising a conjugate consisting of a non-elastase carrier protein and one or more synthetic peptides selected from the group consisting of
NH2-A-V-K-E-G-P-E-Q-V-I-P-I-N-COOH (SEQ ID NO: 2),
NH2-Y-T-N-G-P-L-P-D-K-L-Q-Q-A-R-COOH (SEQ ID NO: 3),
NH2-G-P-L-N-C-P-T-E-D-G-G-W-Q-COOH SEQ ID NO: 4), and
NH2-R-S-G-C-N-G-D-S-G-G-P-L-N-COOH (SEQ ID NO: 5);
wherein said different antibodies are each specific for human pancreatic elastase 1.

6. The diagnostic kit of claim 5 adapted to perform a sandwich enzyme linked immunosorbent assay wherein the kit comprises at least two different antibodies and wherein at least one of the antibodies is solid phase carrier-immobilized and at least one different of the antibodies is detectably labelled.

7. Synthetic peptide A-V-K-E-G-P-E-Q-V-I-P-I-N (SEQ ID NO: 2).

8. Synthetic peptide Y-T-N-G-P-L-P-D-K-L-Q-Q-A-R (SEQ ID NO: 3).

9. Synthetic peptide R-S-G-C-N-G-D-S-G-G-P-L-N (SEQ ID NO: 5).

10. Synthetic peptide G-P-L-N-C-P-T-E-D-G-G-W-Q (SEQ ID NO: 4).

11. A method for obtaining polyclonal or monoclonal antibodies specific for human pancreatic elastase iso-enzyme comprising the steps of:
immunizing a vertebrate animal with an immunogenic composition comprising a conjugate consisting of a non-elastase carrier protein and a peptide, wherein the peptide is selected from the group consisting of:
NH2-A-V-K-E-G-P-E-Q-V-I-P-I-N-COOH (SEQ ID NO: 2)
NH2-Y-T-N-G-P-L-P-D-K-L-Q-Q-A-R-COOH (SEQ ID NO: 3)
NH2-R-S-G-C-N-G-D-S-G-G-P-L-N-COOH (SEQ ID NO: 5)
NH2-G-P-L-N-C-P-T-E-D-G-G-W-Q-COOH SEQ ID NO: 4)
NH2-S-L-Q-Y-E-K-S-G-S-F-Y-COOH (SEQ ID NO: 15)
NH2-F-G-C-N-T-R-R-K-P-T-V-F-T-COOH (SEQ ID NO: 16)
NH2-G-G-E-E-A-R-P-N-S-W-P-W-Q-COOH (SEQ ID NO: 10)
NH2-S-S-S-R-T-Y-R-V-G-L-G-R-H-N-COOH (SEQ ID NO: 11)
NH2-K-D-W-N-S-N-Q-I-S-K-G-N-D-COOH (SEQ ID NO: 12)
NH2-G-P-L-N-C-Q-A-S-D-G-R-W-COOH (SEQ ID NO: 13), and
NH2-G-A-L-P-D-D-L-K-Q-G-R-L-COOH (SEQ ID NO: 14);
thereby inducing formation of the antibodies in the immunized vertebrate animal; and
separating and purifying the formed antibodies from the immunized vertebrate animal to obtain polyclonal antibodies specific for human pancreatic elastase iso-enzyme, or
fusing B-cells from the immunized animal with a myeloma cell line and selecting and cloning hybridoma cell lines to obtain monoclonal antibodies specific for human pancreatic elastase iso-enzyme.

12. The method of claim 11 wherein the vertebrate animal is selected from the group consisting of rabbits, guinea pigs, goats, chicken and fish.

13. The method of claim 12 wherein the vertebrate animal is a chicken.

14. The method of claim 11 wherein the non-elastase carrier protein is selected from hemocyanin or albumin.

15. Isolated and purified polyclonal antibodies specific for a human pancreatic elastase iso-enzyme made by a method comprising the steps of:
immunizing a vertebrate animal with an immunogenic composition comprising a conjugate consisting of a non-elastase carrier protein and a peptide, wherein the peptide is selected from the group consisting of
NH2-A-V-K-E-G-P-E-Q-V-I-P-I-N-COOH (SEQ ID NO: 2),
NH2-Y-T-N-G-P-L-P-D-K-L-Q-Q-A-R-COOH (SEQ ID NO: 3),
NH2-G-P-L-N-C-P-T-E-D-G-G-W-Q-COOH SEQ ID NO: 4),
NH2-R-S-G-C-N-G-D-S-G-G-P-L-N-COOH (SEQ ID NO: 5),
NH2-S-L-Q-Y-E-K-S-G-S-F-Y-COOH (SEQ ID NO: 15),
NH2-F-G-C-N-T-R-R-K-P-T-V-F-T-COOH (SEQ ID NO: 16),
NH2-G-G-E-E-A-R-P-N-S-W-P-W-Q-COOH (SEQ ID NO: 10),
NH2-S-S-S-R-T-Y-R-V-G-L-G-R-H-N-COOH (SEQ ID NO: 11),
NH2-K-D-W-N-S-N-Q-I-S-K-G-N-D-COOH (SEQ ID NO: 12),
NH2-G-P-L-N-C-Q-A-S-D-G-R-W-COOH (SEQ ID NO: 13), and
NH2-G-A-L-P-D-D-L-K-Q-G-R-L-COOH (SEQ ID NO: 14);
thereby inducing formation of the antibodies in the immunized vertebrate animal; and separating and purifying the formed antibodies from the immunized animal to obtain the isolated polyclonal antibodies specific for human pancreatic elastase iso-enzyme.

* * * * *